United States Patent [19]

Barker et al.

[11] Patent Number: 4,754,909

[45] Date of Patent: Jul. 5, 1988

[54] FLEXIBLE STAPLER

[76] Inventors: John M. Barker, 2602 Captains Ave., Port Hueneme, Calif. 93041; Alan K. Plyley, 6837 Sabado Taro, Goleta, Calif. 93117

[21] Appl. No.: 58,759

[22] Filed: Jun. 5, 1987

Related U.S. Application Data

[63] Continuation-in-part of Ser. No. 639,163, Aug. 9, 1984, Pat. No. 4,671,445.

[51] Int. Cl.[4] ............................................. A61B 17/00
[52] U.S. Cl. ................................ 227/19; 227/DIG. 1
[58] Field of Search ........ 128/334 R; 227/19, DIG. 1

[56] References Cited

U.S. PATENT DOCUMENTS

| 2,531,740 | 11/1950 | Orscheln | 74/491 |
|---|---|---|---|
| 4,304,236 | 12/1981 | Conta et al. | 128/325 |
| 4,473,077 | 9/1984 | Noiles et al. | 128/305 |
| 4,485,817 | 12/1984 | Swiggett | 128/334 |
| 4,488,523 | 12/1984 | Shichman | 128/334 |
| 4,580,712 | 4/1986 | Green | 227/19 |
| 4,606,343 | 8/1986 | Conta et al. | 128/305 |
| 4,610,383 | 9/1986 | Rothfuss et al. | 227/19 |
| 4,671,445 | 6/1987 | Barker et al. | 227/19 |

FOREIGN PATENT DOCUMENTS

| 0101310 | 2/1984 | European Pat. Off. . |
| 1057729 | 5/1959 | Fed. Rep. of Germany . |
| WO82/00968 | 4/1982 | PCT Int'l Appl. . |

Primary Examiner—Paul A. Bell
Attorney, Agent, or Firm—Donald M. Sell; James A. Smith; William L. Huebsch

[57] ABSTRACT

A stapler having a spine structure between a staple carrying head assembly and a manually operable actuator assembly that can be made either flexible or rigid as desired during use of the stapler.

22 Claims, 10 Drawing Sheets

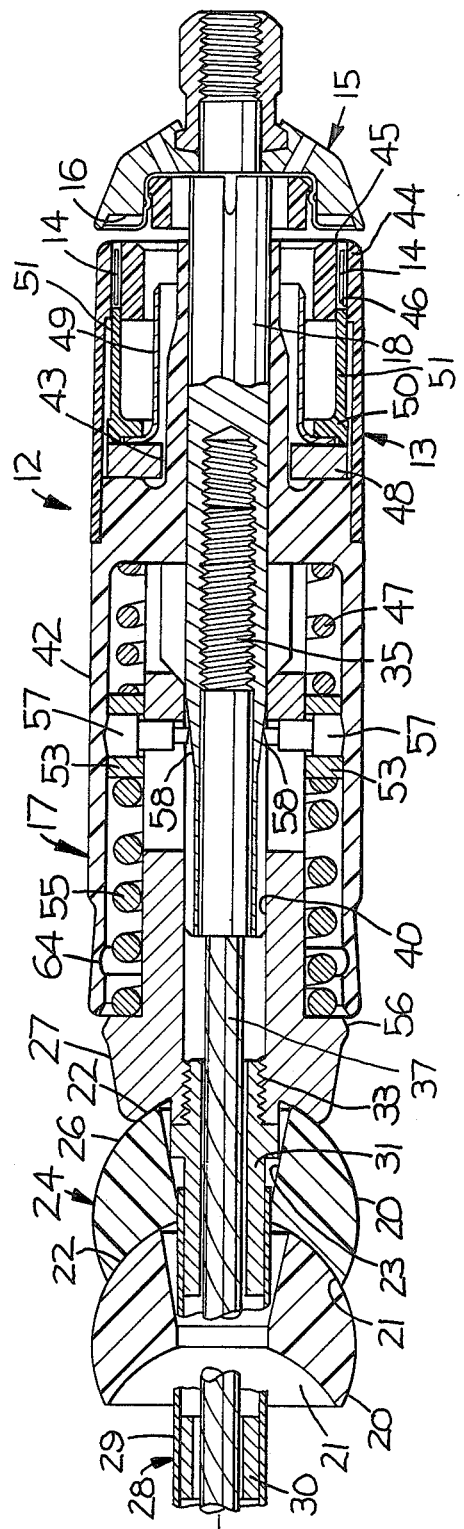
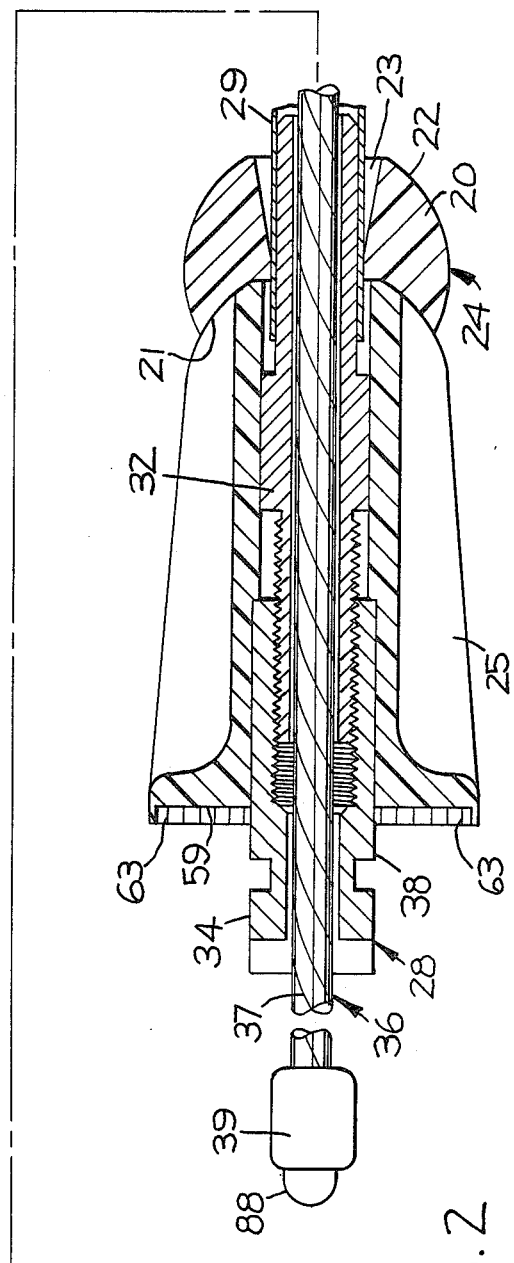
FIG. 2

FLEXIBLE STAPLER

RELATED APPLICATIONS

This is a Continuation in Part of U.S. patent application No. 639,163 filed Aug. 9, 1984, which issued June 9, 1987, as U.S. Pat. No. 4,671,445, the content whereof is incorporated herein by reference.

TECHNICAL FIELD

The present invention relates to surgical staplers adapted to apply one or more rows of staples to staple layers of living tissues together.

BACKGROUND

U.S. patent application No. 639,163 filed Aug. 9, 1984, now U.S. Pat. No. 4,671,445, of which this application is a Continuation in Part, describes staplers adapted for use in stapling together layers of living tissues that have a flexible spine structure between a head assembly in which the staples to be applied are carried, and an actuator assembly that can be manually actuated to apply the staples from the head assembly. That flexible spine structure affords orienting the head and actuator assemblies at different positions relative to each other, which can facilitate using the stapler assembly in certain types of operations.

DISCLOSURE OF INVENTION

The present invention provides a stapler of the type described above which, in addition to having a flexible spine structure that allows a staple carrying head assembly to be positioned at various orientations relative to a manually operable actuator assembly, also allows the spine structure to be rigidified at a selected orientation of the head assembly relative to the actuator assembly which can be useful for manipulating the stapler during various portions of its use in an operation.

According to the present invention there is provided a stapler comprising a head assembly including a staple holding member adapted to hold a plurality of staples in a predetermined pattern, an anvil member having a forming surface adapted to be engaged with staples held in the staple holding member to bend the staples closed, and means mounting the staple holding member and the anvil member for relative movement from at least one spaced position affording the positioning of tissue to be joined between the members toward a closed position to drive the staples through the tissues and bend them closed. Also included in the stapler are a plurality of rigid spine segments, each of which spine segments has a concave end surface, an opposite convex end surface, and a through opening between the end surfaces. The spine segments are disposed in end to end relationship with their openings aligned and the concave and convex surfaces of adjacent spine segments in engagement to form the spine structure extending from a first end to a second end abutting one of the members in the head assembly. A flexible stiffening assembly having a through passageway extends through the aligned openings in the spine segments of the spine structure, which stiffening assembly has a second end attached to the member abutted by the spine structure, and a first end adjacent the first end of the spine structure; and a flexible cable assembly extends through the passageway in the stiffening assembly, which cable assembly has a second end attached to the member not abutted by the spine structure, and a first end adjacent the first end of the spine structure. An actuating assembly is also included in the stapler and includes a frame abutting the first end of the spine structure; manually activatable tension applying means engaging the first end of the stiffening assembly and mounted on the frame for movement from a disengaged position at which sufficient slack is provided in the stiffening assembly to afford flexing of the spine structure to orient the spine segments and thereby the head assembly at a desired orientation relative to the actuator assembly, to an engaged position at which tension is applied to the first end of the stiffening assembly relative to the frame to compress the spine segments between the member abutting the second end of the spine structure and the frame and thereby rigidify the spine structure; and manually actuatable member operating means including means engaging the first end of the cable assembly and mounted on the frame for movement from an open position to position the staple holding and anvil members at their spaced positions, to a closed position to move those members to their closed position.

Preferably, the head assembly together with the spine structure, stiffening assembly and cable assembly are made as a disposable subassembly intended for a single use, whereas the manually operable actuating assembly is re-usable and adapted for releasable engagement with the disposable subassembly.

BRIEF DESCRIPTION OF DRAWING

The present invention will be further described with reference to the accompanying drawing wherein like reference numerals refer to like parts in the several views, and wherein:

FIG. 2 is an enlarged fragmentary sectional side view of a stapler subassembly included in the stapler of FIG. 1;

DETAILED DESCRIPTION

Figure 1:
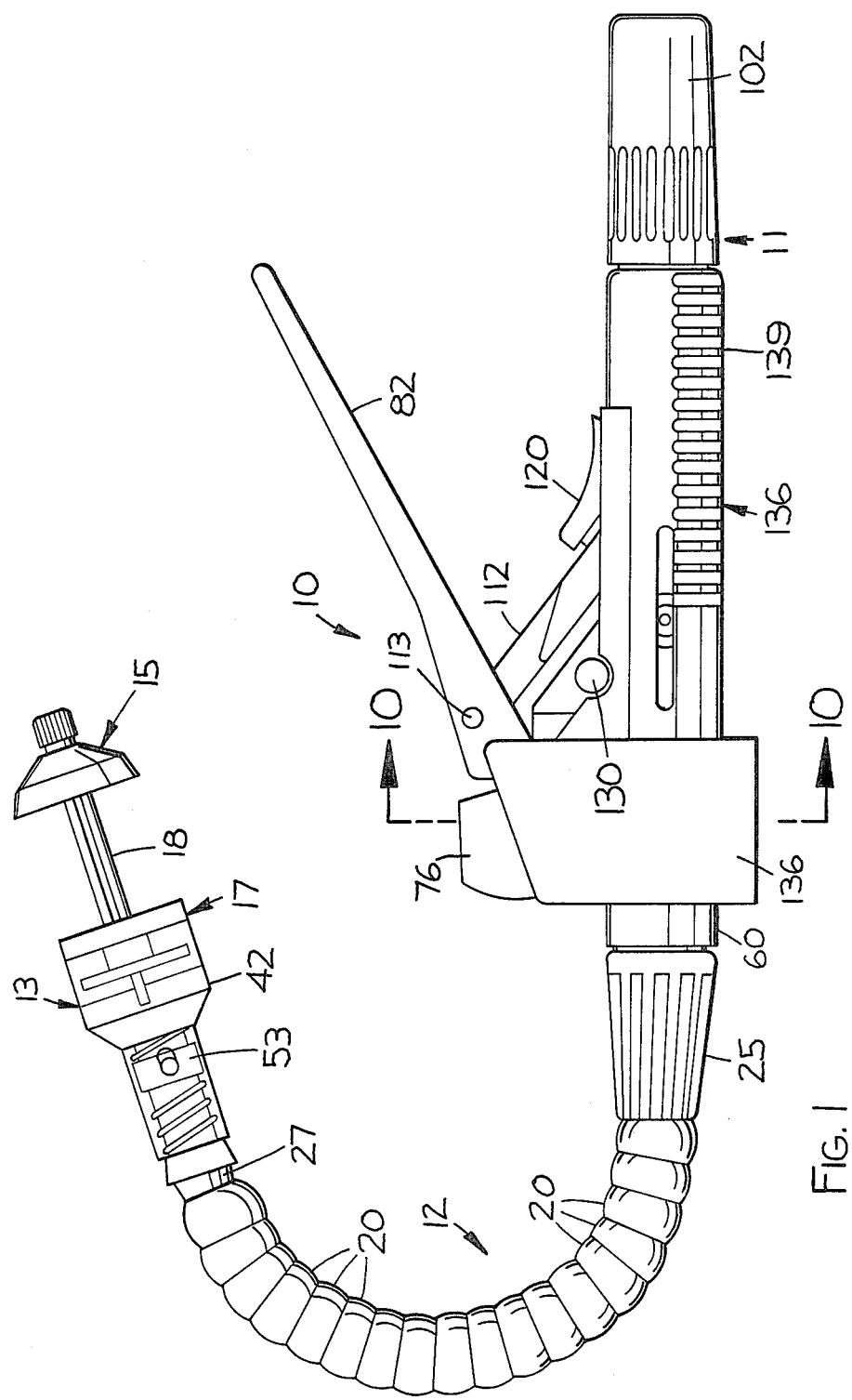
FIG. 1 is a side view of a stapler according to the present invention.

Referring now to the drawing, there is shown a stapler 10 according to the present invention including a manually actuatable actuator assembly 11, and a stapler subassembly 12.

Figure 9:
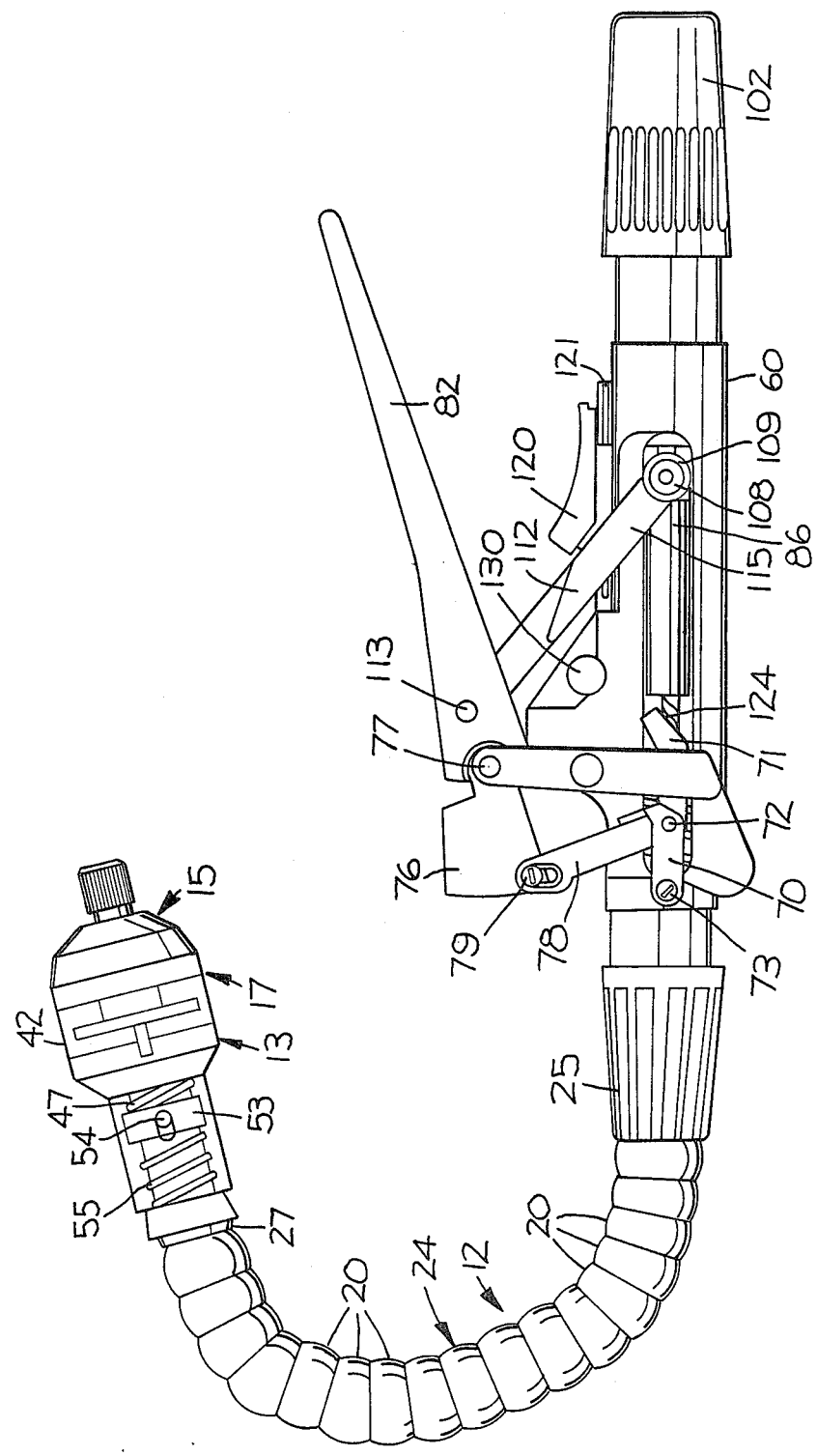

Generally the stapler subassembly 12 comprises a head assembly 17 including a staple holding assembly or member 13 FIG. 2 adapted to hold a plurality of staples 14 in a predetermined pattern, an anvil assembly or member 15 having a forming surface 16 adapted to be engaged with the staples 14 held in the staple holding assembly 13 to bend the staples 14 closed, and means in the form of a rod 18 axially slidably mounted in a bore through the staple holding assembly 13 mounting the staple holding assembly 13 and the anvil assembly 15 for relative movement from various spaced positions (FIGS. 1, 2 and 4-8) affording the positioning of tissue to be joined (e.g., the adjacent ends of a severed human bowel) between the assemblies 13 and 15, toward a closed position (FIG. 9) to drive the staples 14 through the tissues and bend them closed.

The stapler subassembly 12 further includes a plurality of rigid spine segments 20, each of which spine segments 20 has a concave end surface 21, FIG. 2 an opposite convex end surface 22, and a frustoconical through opening 23 between the end surfaces 21 and 22. The spine segments 20 are disposed in end to end relationship with their openings 23 aligned and the concave and convex 21 and 22 surfaces of adjacent spine segments 20 in engagement to form a spine structure 24 extending from a first end defined by a frustoconical member 25 having a convex end surface engaging the concave end surface 21 of the adjacent spine segment 20 to a second end 26 abutting a base member 27 in the staple holding assembly 13. The stapler subassembly 12 further includes a flexible stiffening assembly 28 comprising a woven wire sleeve 29 supported on a plurality of spaced rigid cylindrical support members 30, end fittings 31 and 32 with through openings, and an end piece 38 threadably engaged with the end fitting 32 to afford adjusting the effective length of the stiffening assembly 28 during manufacture of the subassembly 12 that also has a through opening so that the flexible stiffening assembly 28 has a through passageway. The stiffening assembly 28 extends through the aligned openings 23 in the spine segments 20 of the spine structure 24, has a second end defined by the fitting 31 attached by threads 33 on the fitting 31 to the base member 27, and a first end defined by the end piece 38 which has an annular collar 34 at its end adjacent the first end 25 of the spine structure 24 adapted to be tensioned relative to the spine structure 24 to afford compressing the spine segments 20 of the spine structure 24 together to rigidify the spine structure 24. A flexible cable assembly 36 extends through the passageway in the stiffening assembly 28. The cable assembly 36 includes a woven wire cable 37, has a rigid threaded end portion 35 fixed to the cable 37 at a second end which is threadably engaged in the rod 18 to afford adjusting the effective length of the cable assembly 36 during manufacture of the subassembly 12, and a cylindrical lug 39 attached at a first end of the cable 37 adjacent the first end 25 of the spine structure 24 adapted to be pulled relative to the spine structure 24 to move the staple holding and anvil assemblies 13 and 15 through their various spaced positions to their closed position.

Figure 11:
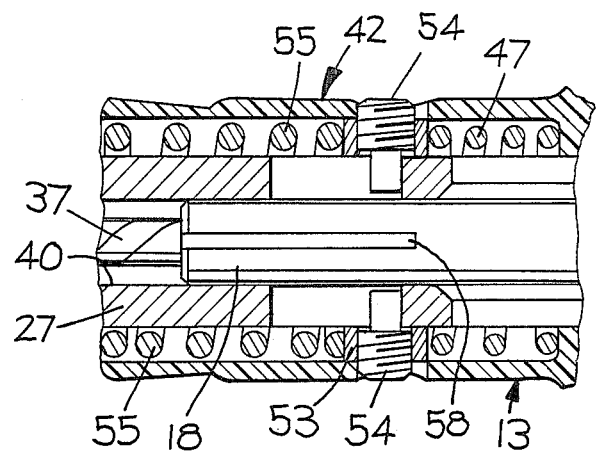
FIG. 11 is a fragmentary sectional view of a head assembly included in the stapler of FIG. 1 taken at a right angle to the view of FIG. 2.

The staple holding assembly 13 FIG. 2 comprises the base member 27 having a concave surface with which the convex surface 22 on the adjacent spine segment 20 in the spine structure 24 is engaged and with which the threads 33 on the end fitting 31 are engaged, and which provides a bearing surface 40 for the end of the rod 18 included in the anvil assembly 15 to which the cable assembly 36 is attached. Also included in the staple holding assembly 13 is a two part clear plastic housing 42, the parts of which are held together by hooks on one (not shown) that automatically engage openings on the other part when the parts are assembled. The housing 42 has an inner cylindrical wall 43 slidably mounted on the outer surface of the rod 18 and an end wall 44 having an annular end surface 45 opposite the base member 27 portion with inner and outer concentric rows of passageways 46 opening through the end surface 45, in which passageways 46 are positioned a plurality of the generally U-shaped staples 14 having spaced generally parallel leg portions projecting from the ends of central portions at the ends of the leg portions opposite the end surface 45. The housing 42 has a central generally cylindrical cavity in which are located a support washer 48 having a surface adjacent the end wall 44 on which are supported a flange on one end of a cylindrical knife 49 having an end cutting edge adapted to cut a clean central opening through tissues being stapled, and a base ring of a pusher member 50 from which project a plurality of projections 51 having end portions in the passageways 46 supporting the central portions of the staples 14. The housing 42 can move relative to the support washer 48, knife 49 and pusher member 50 a distance sufficient for the end wall 44 to move along the projections 51 so that the staples 14 are exposed so that they can be embedded in tissue between the projections 51 and the anvil assembly 15. The side of the support washer 48 opposite the pusher member 50 is positioned adjacent the end of the base member 27 opposite the spine structure 24 assembly and shaped so that it and the knife 49 and the projections 51 can not move past the base member 27 when the anvil assembly 15 is moved toward the base member 27 by the cable assembly 36. When thick tissue is positioned and compressed between the end surface 45 of housing 42 and the anvil assembly 15 by movement of the anvil assembly 15 toward the housing 42, the housing 42 can move against the bias of a relatively light space adjustment spring 47 between the housing and a collar 53 slidably mounted around the base member 27 a short distance equal to the lengths of slots in the housing 42 (FIG. 11) receiving pins 54 engaged in the collar 53, which pins 54 have inner ends slidably received in guide slots in the base member 27. Thereafter, further movement of the housing 42 due to compression of the tissue between the anvil assembly 15 and housing 42 requires movement of the collar 53 with the housing 42 (due to engagement of the pins 54 with the ends of the slots in the housing 42) against a relatively heavy pre-load spring 55 between the collar 53 and the base member 27. Such movement of the housing 42 toward the base member 27 will cause engagement between an end of the housing 42 and a lip 56 on the base member 27 which produces substantial resistance to further movement of the housing 42 relative to the base member 27 at a position with the staples 14 still within the passageways 46. This resistance between the housing 42 and lip 56 is overcome when the radially inwardly projecting ends of drive pins 57 fixed in the collar 54 are engaged by the end walls 58 of slots in the rod 18 (FIG. 2) as the anvil assembly 15 is pulled toward the base member 27 by the cable assembly 36 (at which time a predetermined spacing exists between the end surface 45 and anvil assembly 15 in which the tissue is compressed, called herein a predetermined spaced position between the staple holding assembly 13 and the anvil assembly 15), after which the housing 42 is moved back with the anvil assembly 15 by engagement of the end walls 58 on the rod 18 with the drive pins 57 in the collar 53 and the pins 54 in the collar 53 with the housing 42 so that the end of the housing 42 is forced over the lip 56 on the base member 27 (which lip 56 has a heavy interference fit with the housing 42) and moves to a position with a recess 64 around the inner surface of the housing 42 adjacent the lip 56 while producing a clearly audible snapping sound; and tissue between the anvil assembly 15 and housing 42 is then moved onto the ends of the staples 14 on the projections 51 (which staples 14 are supported by the end of the base member 27 and thus do not move with the housing 42) and the staples 14 are bent closed by contact with the forming surface 16 of the anvil assembly 15 as the staple holding assembly 13 and the anvil assembly 15 reach what is called a closed position herein at which the knife 49 has also cut out a central portion of the stapled tissue.

Figure 4:
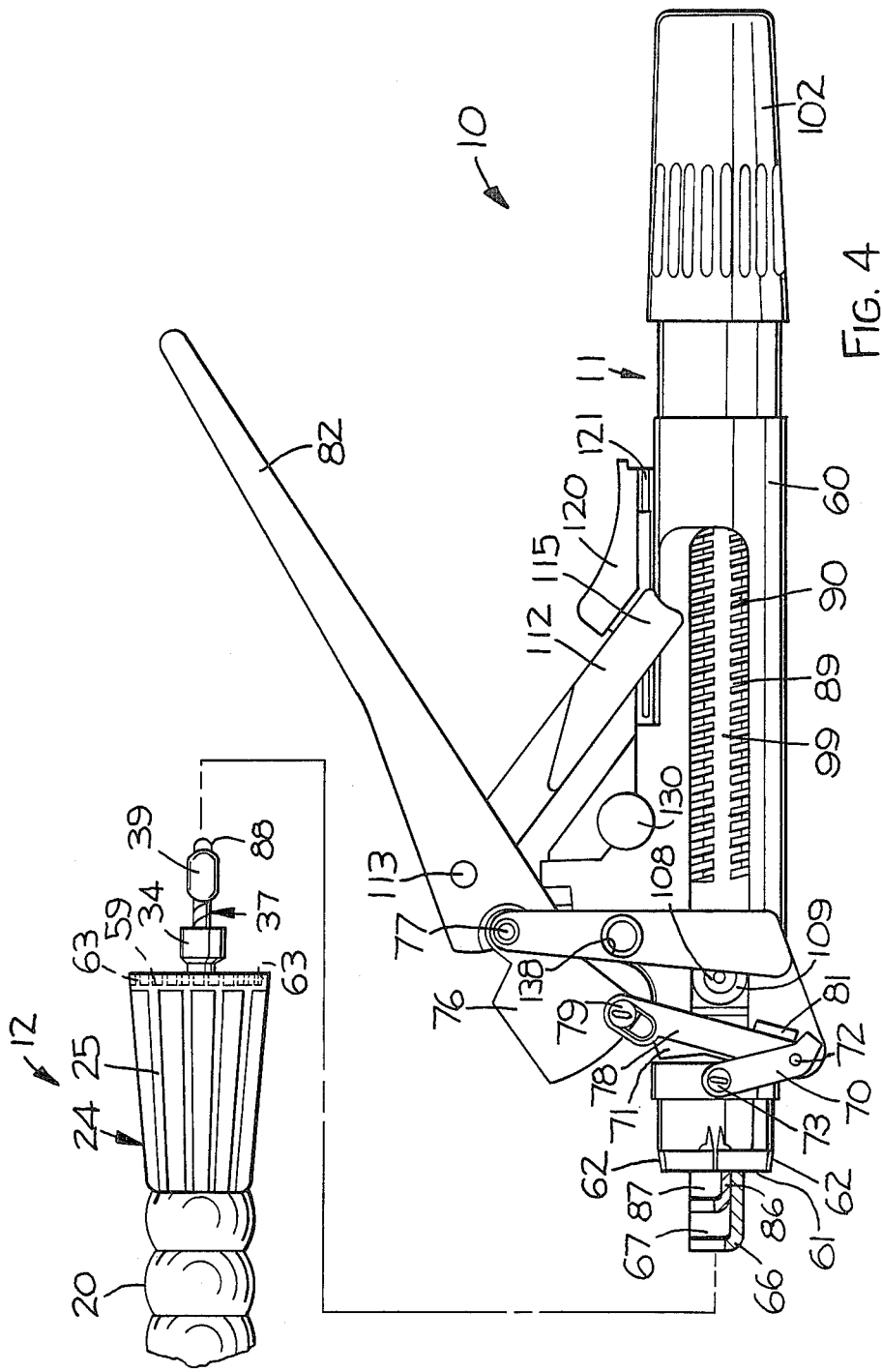
FIGS. 4 through 9 are side views of the stapler of FIG. 1 having an enclosure removed to show the relative positions of parts thereof during use of the stapler.

The actuator assembly 11 for use with the stapler subassembly 12 comprises a frame 60 which has a projecting annular abutment portion 61 FIG. 4 adapted to abut a distal end surface 59 of the frustoconical member 25 of the spine structure 24 and has external teeth 62 adapted to engage different ones of a ring of inwardly projecting teeth 63 FIG. 2 on that end of the frustoconical member 25 to afford orienting the stapler subassembly 12 at various rotational positions relative to the actuator assembly 11 which facilitates assembly of the actuator assembly 11 and stapler subassembly 12, allows the user to apply torque to the head assembly 17 from the actuator assembly which is useful in inserting or removing the head assembly 17, and also is useful with different types of stapler subassemblies of the type illustrated in the parent application that apply staples in different patterns such as a linear pattern to provide various orientations between the actuator assembly 11 and the staple pattern.

Also included in the actuator assembly 11 are manually activatable tension applying means adapted to releasably engage the annular collar 34 at the first end of the stiffening assembly 28. The manually activatable tension applying means are mounted on the frame 60 for movement from a disengaged position at which sufficient slack is provided in the stiffening assembly 28 to afford flexing of the spine structure 24 to orient the spine segments 20 and thereby the head assembly 17 at a desired orientation relative to the actuator assembly 11, to an engaged position at which tension is applied to the first end of the stiffening assembly 28 relative to the frame 60 to compress the spine segments 20 between the base member 27 of the staple holding assembly 13 and the frame 60 to thereby rigidify the spine structure 24; and manually actuatable head assembly 17 operating means including means adapted for releasably engaging the cylindrical lug 39 at the first end of the cable assembly 36 are mounted on the frame 60 for movement from various open positions to position the staple holding and anvil assemblies 13 and 15 at their various spaced positions, to a closed position to move the staple holding and anvil assemblies 13 and 15 to their closed position.

Figure 3:
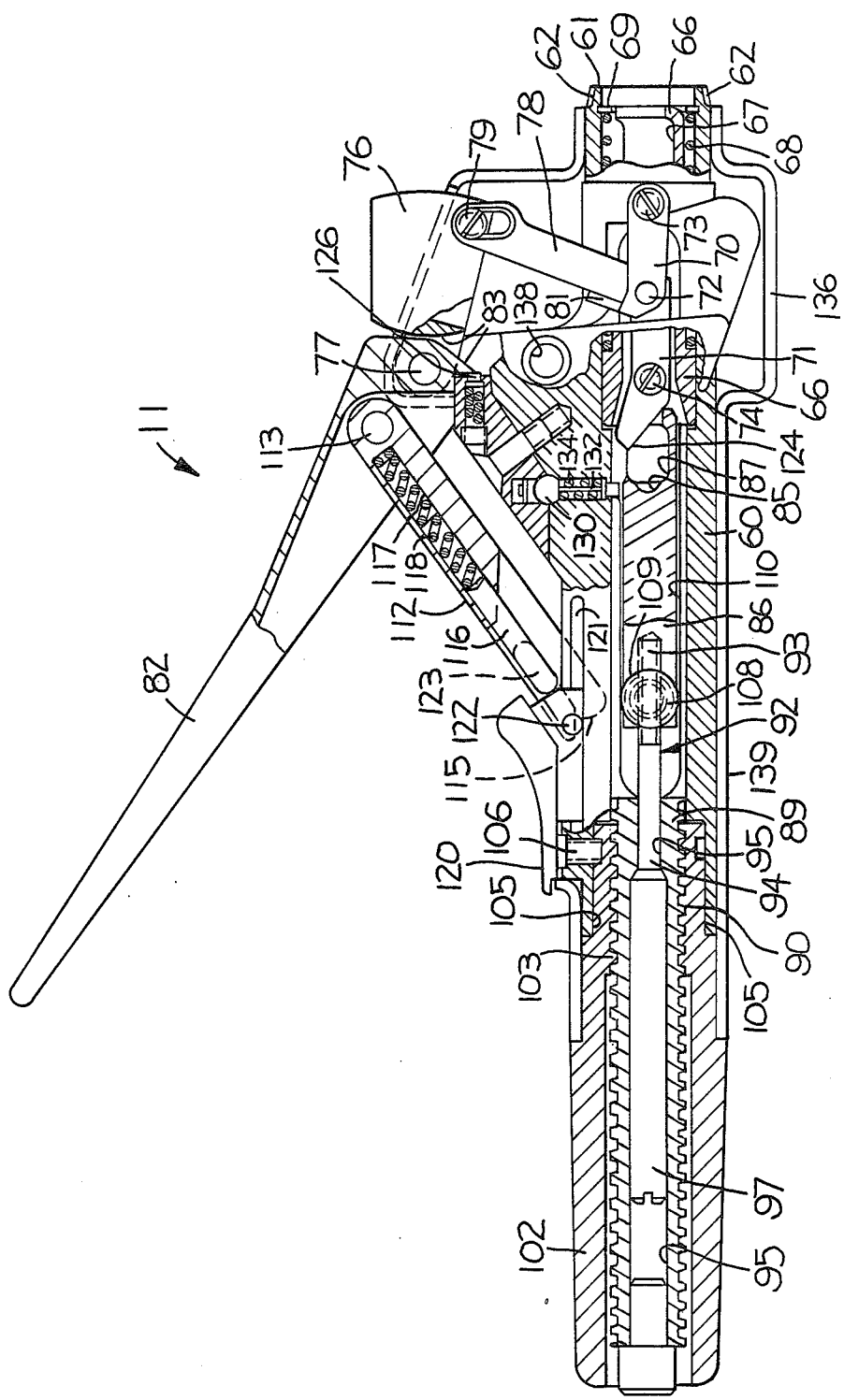
FIG. 3 is an enlarged sectional side view of an actuator assembly included in the stapler of FIG. 1.
Figure 10:
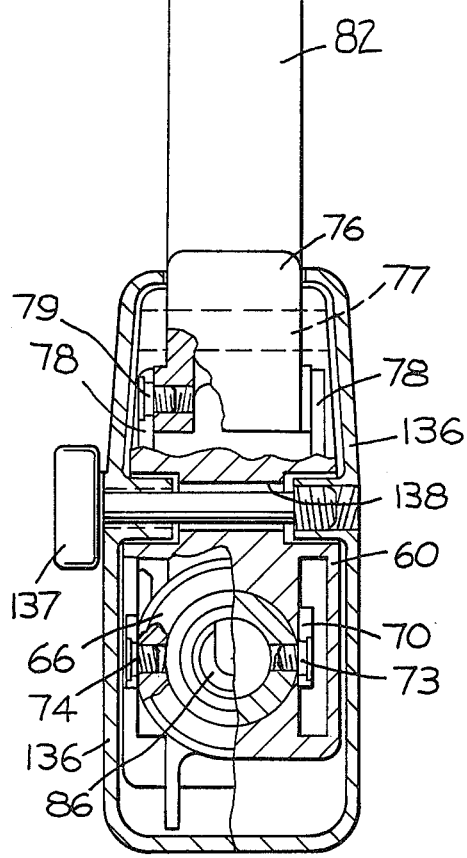
FIG. 10 is an enlarged sectional view taken approximately along line 10—10 of FIG. 1, and having parts broken away to show detail.

The manually activatable tension applying means adapted to releasably engage the annular collar 34 at the first end of the stiffening assembly 28 comprises a piston 66 (FIGS. 3, 4 and 10,) and walls defining a side opening receptacle 67 adapted to receive the annular collar 34 with the passageway in the stiffening assembly 28 aligned with the axis of the piston 66. The walls defining the receptacle 67 prevent movement of the annular collar 34 axially of the piston 66 when the annular collar 34 is in the receptacle 67. The frame 60 has a socket opening through the annular portion 61 of the frame 60 adapted to abut the spine structure 24, which socket receives the piston 66 for axial movement within the socket from a release position (FIG. 4) with the walls of the piston 66 defining the receptacle 67 projecting from the frame 60 to afford access to the receptacle 67, to various engaged positions (FIGS. 3 and 5-9) to which the piston 66 is biased by a spring 68 between a snap ring 69 engaged with the frame 60 and the piston 66 with the walls of the piston 66 defining the receptacle 67 within the socket so that the annular collar 34 is retained in the receptacle 67.

The manually activatable tension applying means engaging the annular collar 34 at the first end of the stiffening assembly 28 and mounted on the frame 60 for movement from a disengaged position at which sufficient slack is provided in the stiffening assembly 28 to afford flexing of the spine structure 24 to orient the spine segments 20 and thereby the head assembly 17 at a desired orientation relative to the actuator assembly 11, to an engaged position at which tension is applied to the annular collar 34 at the first end of the stiffening assembly 28 relative to the frame 60 to compress the spine segments 20 between the base member 27 of the staple holding assembly 13 abutting the second end of the spine structure 24 and the frame 60 to thereby rigidify the spine structure 24 comprises the piston 66 and two pairs of toggle members 70 and 71. Each pair of the toggle members 70 and 71 has first ends pivotably attached together by a pin 72, and opposite second ends with the second end of the toggle member 70 pivotably mounted on the frame 60 at a pin 73, and the second end of the toggle member 71 pivotably mounted on the piston 66 at a pin 74. The pairs of toggle members 70 and 71 provide toggle joint linkages that are mounted for movement between various release positions (FIGS. 4 and 5) with the pivotably mounted first and second ends of the toggle members 70 and 71 out of alignment to afford movement of the piston 66 between its release position and its engaged positions, to an engaged position (FIGS. 6-9) with the pivotably mounted first and second ends of the toggle members 70 and 71 generally aligned to forcibly move the piston 66 to a tensioning position at which tension is applied to the stiffening assembly 28 through the annular collar 34. A release member 76 is mounted on the frame 60 for pivotable motion about a pin 77. A pair of actuating links 78 have first ends pivotably attached to the toggle members 70 and 71 at the pins 72 and second ends pivotably and slidably mounted on the release member at pins 79 spaced from the pin 77 that engage slots in the actuating links 78. The release member 76 is pivotable about the pin 77 between an engaged position at which the release member 76 through the actuating links 78 positions the toggle members 70 and 71 in their engaged position defined by stop ledges 81 on the edges of the actuating links 78 engaged by projecting first ends of the toggle members 70, and various release positions past center for the toggle members 70 and 71 from their engaged position to which release positions the toggle members 70 and 71 may be pushed from their engaged positions by the release member 76 through the actuating links 78. The walls of the slots in the actuating links 78 engaged by the pins 79 provide a camming action and thereby a mechanical advantage to move the toggle members 70 and 71 from their engaged position so that greater travel but less force is required by the release member 76 to do so. A manually operable actuating lever 82 is mounted on the frame 60 for pivotable movement about the pin 77 between a normal position (FIGS. 5, 7 and 8) and an actuated position (FIGS. 6 and 9); and means in the form of contact surfaces 83 adapted for engagement between the actuating lever 82 and the release member 76 only when the actuating lever 82 is moved to its actuating position when the release member 76 is originally in its release position are provided for moving the release member 76 to its engaged position upon movement of the actuating lever 82 from its normal position to its actuated position, for affording retention of the release member 76 in its engaged position upon movement of the actuating lever 82 from its the actuated position to its normal position, and for affording free movement of the release member 76 between its engaged and release positions when the actuating lever 82 is in its normal position.

The manually actuatable head assembly 17 operating means including means adapted for releasably engaging the cylindrical lug 39 at the first end of the cable assembly 36 and mounted on the frame 60 for movement from open positions to position the staple holding assembly 13 and anvil assembly 15 at their spaced positions, to a closed position to move the staple holding assembly 13 and anvil assembly 15 to their closed position comprises an elongate carrier 86 and walls defining a side opening recess 87 adapted to receive the cylindrical lug 39 with a tip 88 on the cable received in a cup-like receptacle 85 in a rear one of the walls and the activating cable 36 aligned with its axis and to prevent movement of the cylindrical lug 39 radially of the carrier 86 when the cylindrical lug 39 is in the recess 87. Means including the piston 66 and portions of the frame 60 define a passageway adapted to receive the carrier 86, which passageway opens through the annular portion 61 of the frame 60 adapted to abut the spine structure 24. The carrier 86 is mounted for axial movement within the passageway from a release position (FIG. 4) with the walls of the carrier 86 defining the recess 87 projecting from the passageway to afford access to the recess 87 in the carrier 86, to various engaged positions (FIGS. 5-9) with the walls of the carrier 86 defining the recess 87 within the means defining the passageway so that the cylindrical lug 39 is retained in the recess 87. The engaged positions for the carrier 86 include various open positions affording positioning the staple holding and anvil assemblies 13 and 15 at various spaced positions to afford positioning tissues therebetween, a ready position adapted to position the staple holding and anvil assemblies 13 and 15 at the predetermined spaced position, and a final position adapted to position the the staple holding and anvil assemblies 13 and 15 at their closed position. Manually activatable means for positioning the carrier 86 in its release and engaged positions includes an anchor member 89 having an axis and threads 90 about its periphery along the axis. The anchor member 89 is mounted on the frame 60 for free axial sliding movement along a path axially aligned with the carrier 86 at the end of the carrier 86 opposite the recess 87. Relative movement limiting means in engagement between the carrier 86 and the anchor member 89 are provided by a screw 92 FIG. 3 having a threaded end 93 threadably engaged with the end of the carrier 86 opposite the recess 87, a central stem 94 slidable in a small diameter portion of a central bore 95 through the carrier 86, and an elongate slotted head 97 longitudinally movable in a larger diameter portion of the bore 95 are provided for affording limited relative axial movement between the carrier 86 and the anchor member 89 over a distance about equal to the distance between the ready and final positions of the carrier 86, which distance is defined by the distance between the screw head 97 and the small diameter portion of the bore 95 when the carrier 86 and anchor member 89 abut each other. Means in the form of flatted opposite sides 99 of the anchor member 89 slidable in a correspondingly shaped opening in in the frame 60 are provided for preventing rotation of the anchor member 89 relative to the frame 60. An adjustment knob 102 having an axis and a through bore around the axis partially defined by internal threads 103 in engagement with the threads 90 on the anchor member 89 is mounted on the frame 60 for manual rotation about its axis without axial movement of the adjustment knob 102 relative to the frame 60 by means including cylindrical bearing surfaces 105 therebetween, and a pin 106 fixed in the frame 60 and projecting into a groove around the adjustment knob 102. The adjustment knob 102 is manually rotatable to move the anchor member 89 from a first position at which the movement limiting means or screw 92 affords movement of the carrier 86 between its ready and final positions, to second positions to thereby move the carrier 86 to its open and released positions, and manually activatable pressure applying means mounted on the frame 60 are adapted for engaging the carrier 86 in the ready position when the anchor member 89 is in the first position and for moving the carrier 86 from the ready position to the final position to move the the staple holding and anvil assemblies 13 and 15 to their closed position.

The manually activatable pressure applying means mounted on the frame 60 adapted for engaging the carrier 86 in the ready position when the anchor member 89 is in the first position and for moving the carrier 86 from the ready position to the final position to move the the staple holding and anvil assemblies 13 and 15 to their closed position comprises a pair of opposite outwardly projecting bosses 108 on the carrier 86 having wheels 109 rotatably mounted at their outer ends that are adapted to roll along an underlying surfaces 110 on the frame 60, the actuating lever 82, a bifurcated yoke 112 having a first end portion pivotably mounted at a pin 113 on the actuating lever 82 spaced from the pin 77 about which the actuating lever 82 pivots, two second end portions 115 adapted to engage the bosses 108, and means for guiding the second end portions 115 that are manually movable between a non-stapling position (FIGS. 4-7) spaced from the bosses 108, and a stapling position (FIGS. 8 and 9) aligned with the bosses 108 to move the carrier 86 from the ready position (FIG. 8) to the final position (FIG. 9) upon movement of the actuating lever 82 from its normal to its actuated position. The means for guiding comprises a manually operable slide 120 slidably mounted in grooves 121 on the frame 60, and having two outwardly projecting pins 122 FIG. 3 slidably engaged in longitudinal slots 123 along the inner sides of the end portions 115 of the yoke 112 so that manual movement of the slide 120 moves the means for guiding between the stapling and non-stapling positions described above. Means are provided for biasing the slide 120 to its nonstapling position in the form of a rod 116, and a channel 117 in the yoke 112 receiving a first end portion of the rod 116 for axial sliding movement and which contains a spring 118 biasing the rod 116 out of the channel 117 with the end of the rod 116 opposite the spring 118 pressed against the adjacent surface of the slide 120. Movement of the second end portions 115 to their stapling position is also facilitated by an outwardly spring loaded stop plunger 126 that in its normal outer position determines the normal position of the acuating lever 82, but can be forced inwardly to allow the lever 82 to move past its normal position during movement of the end portions 115 onto the bosses 108.

Figure 5:
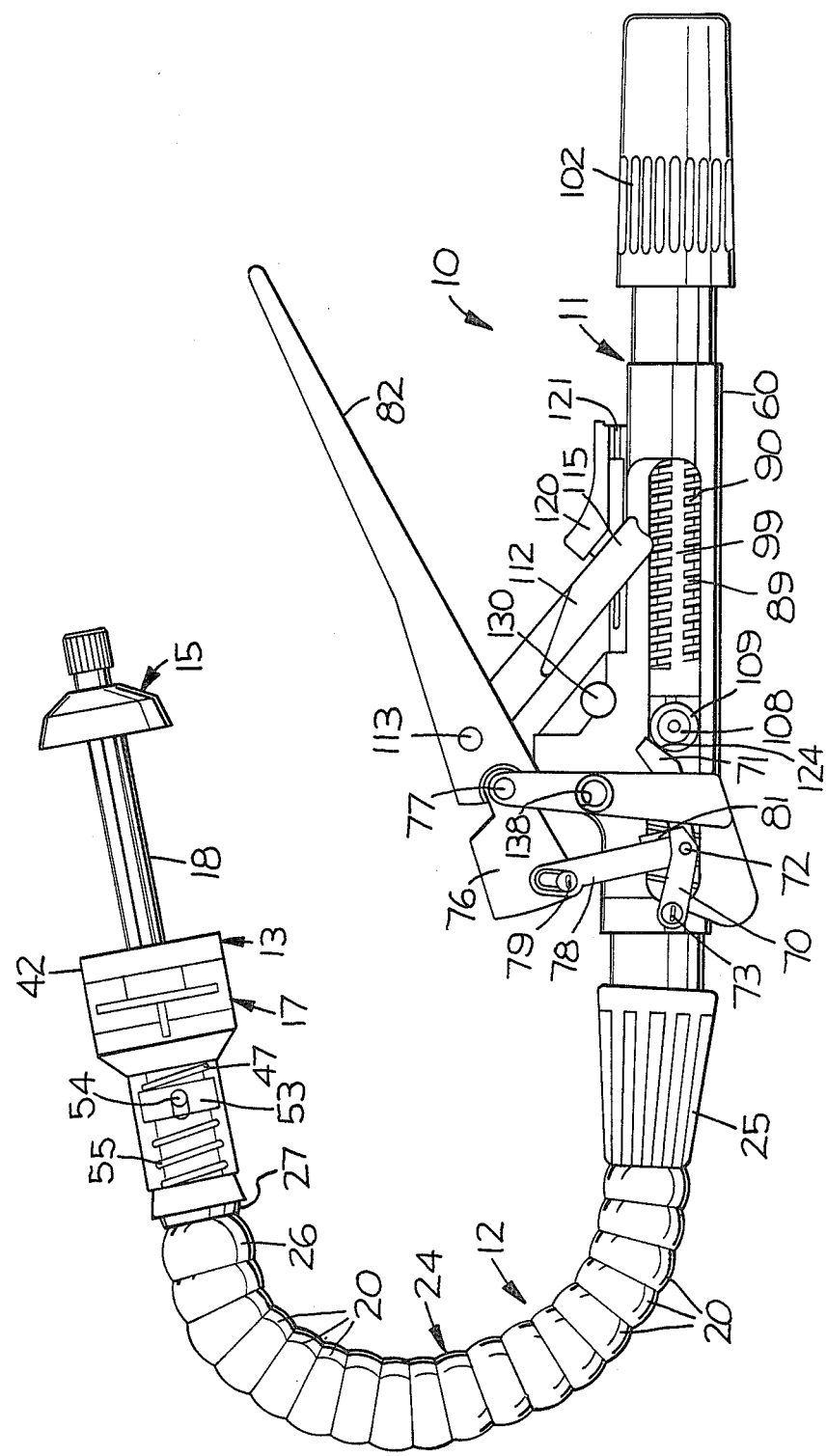

The actuator assembly 11 further including means for moving the toggle members 70 and 71 to their release positions from their engaged position during movement of the carrier 86 from its engaged positions to its release position provided by cam surfaces 124 on the second ends of the toggle members 71 adapted for engagement by the wheels 109 included in the bosses 108 (FIG. 5). Such engagement insures that the toggle members 70 and 71 are in their release positions to allow movement of the piston 66 to its release position when the piston 66 is abutted by the carrier 86 as the carrier 86 is moved to its release position by rotation of the adjustment knob 102.

The actuator assembly 11 further includes manually releasable means for preventing movement of the carrier 86 from its engaged positions to its release position by operation of the adjustment knob 102 to restrict inadvertent movement of the carrier 86 and piston 66 to their release positions, which could present a problem during an operation. These means comprise a safety button 130 mounted on the frame 60 for movement transverse of the anchor member 89 between a normal position at which a cam surfaces on the safety button 130 and a safety pin 132 mounted in the frame 60 for movement in a direction at right angles to the direction of movement of the safety button 130 position the safety pin 132 at a blocking position with its end in the path for the anchor member 89 at approximately the location the anchor member 89 pushes the carrier 86 from its last engaged position to its release position, and to which normal and blocking positions the safety button 130 and safety pin 132 are biased by a spring 134 around the safety pin 132. The cam surfaces on the safety button 130 and the safety pin 132 will move the safety pin 132 from its blocking position to a release position retracted from the path for the anchor member 89 when the safety button 130 is manually depressed to afford movement of the anchor member 89 to its release position by operation of the adjustment knob 102.

A metal two part enclosure 136 (FIGS. 1, 3 and 10) normally surrounds the mechanism of the actuator assembly 11, is held in place by a thumb screw 137 passing through an opening 138 in the frame 60, and provides a cylindrical handle 139 for the actuator assembly 11 adjacent the adjustment knob 102 and actuating lever 82.

OPERATION

Figure 6:
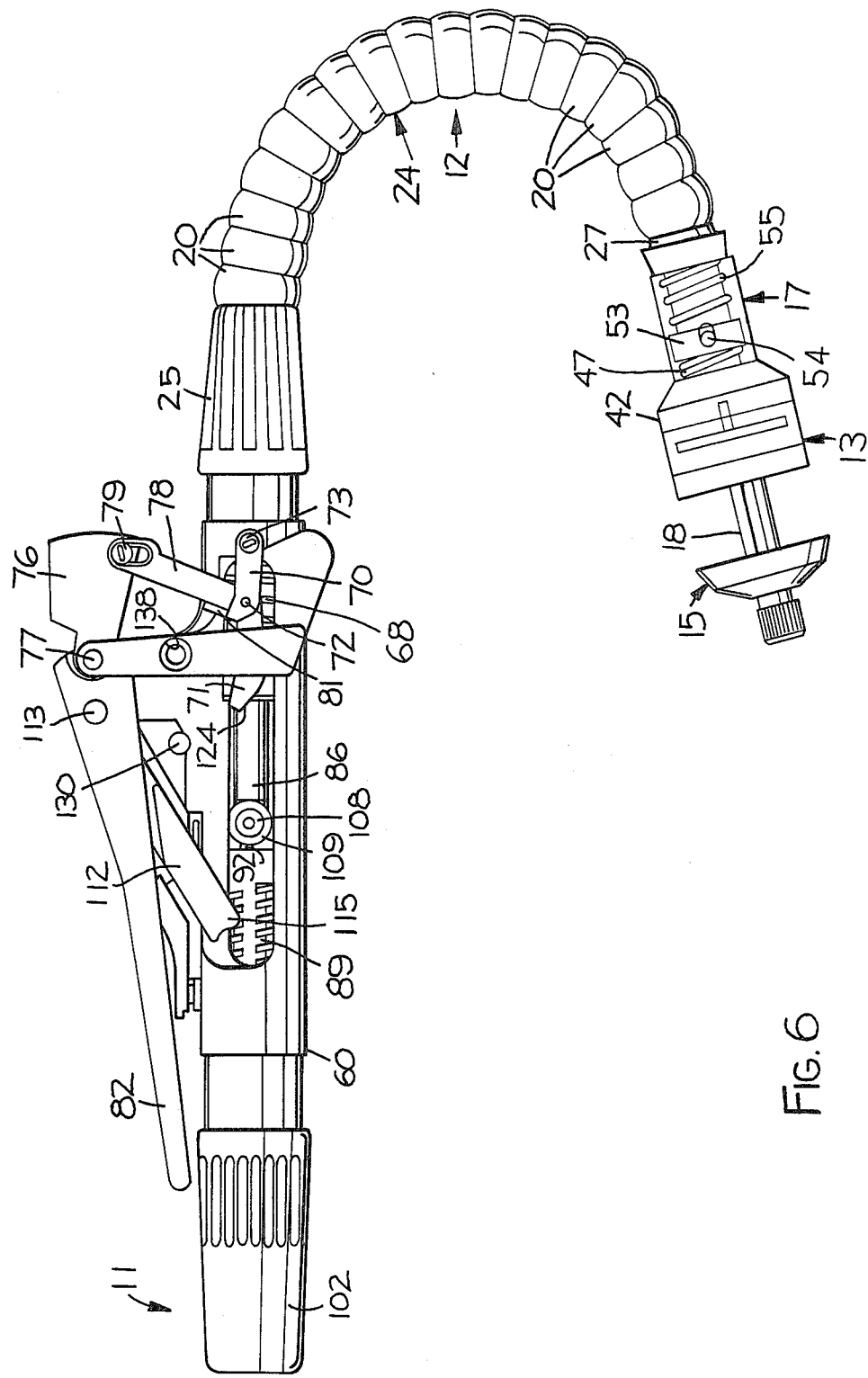
Figure 7:
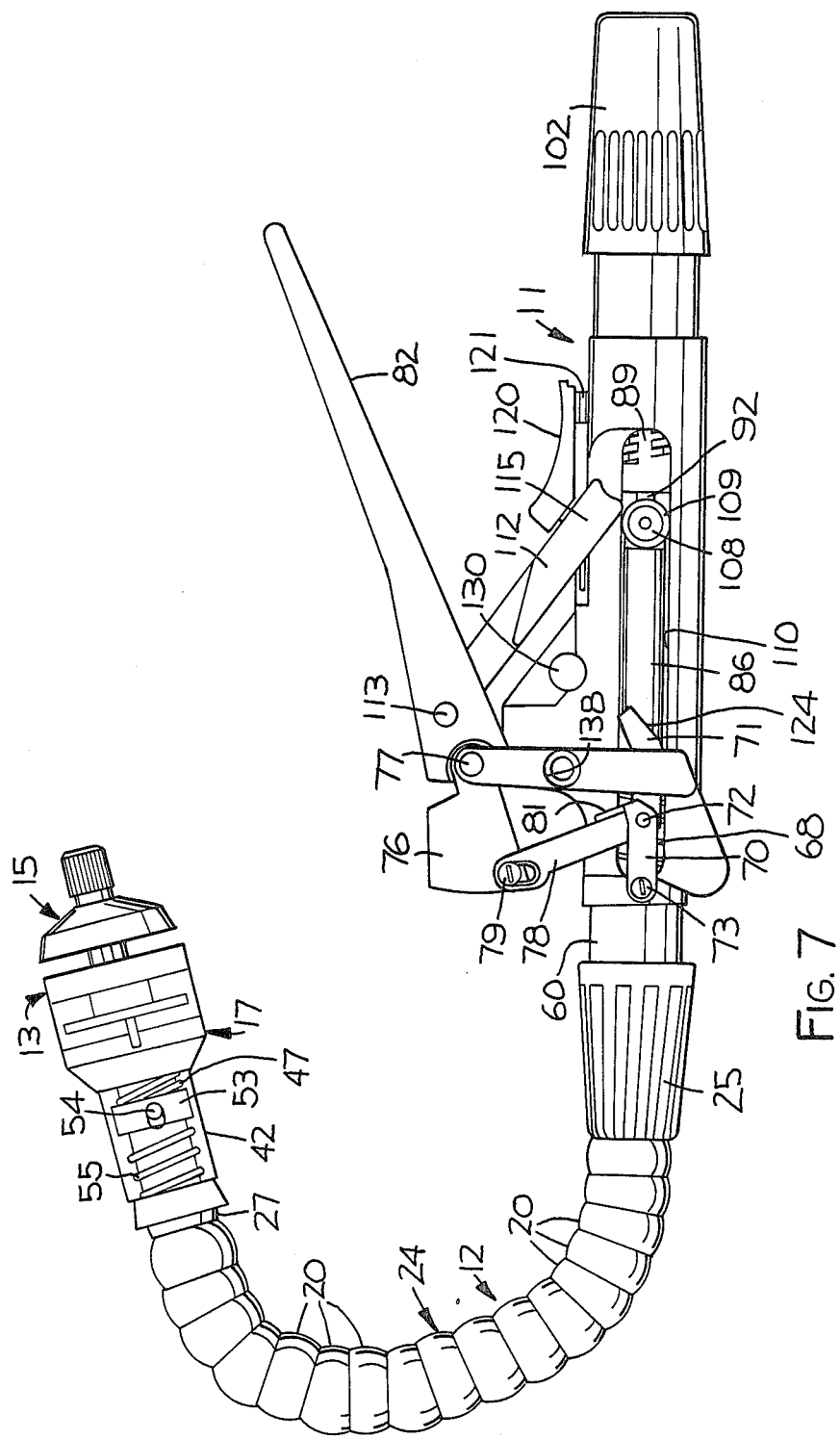
Figure 8:
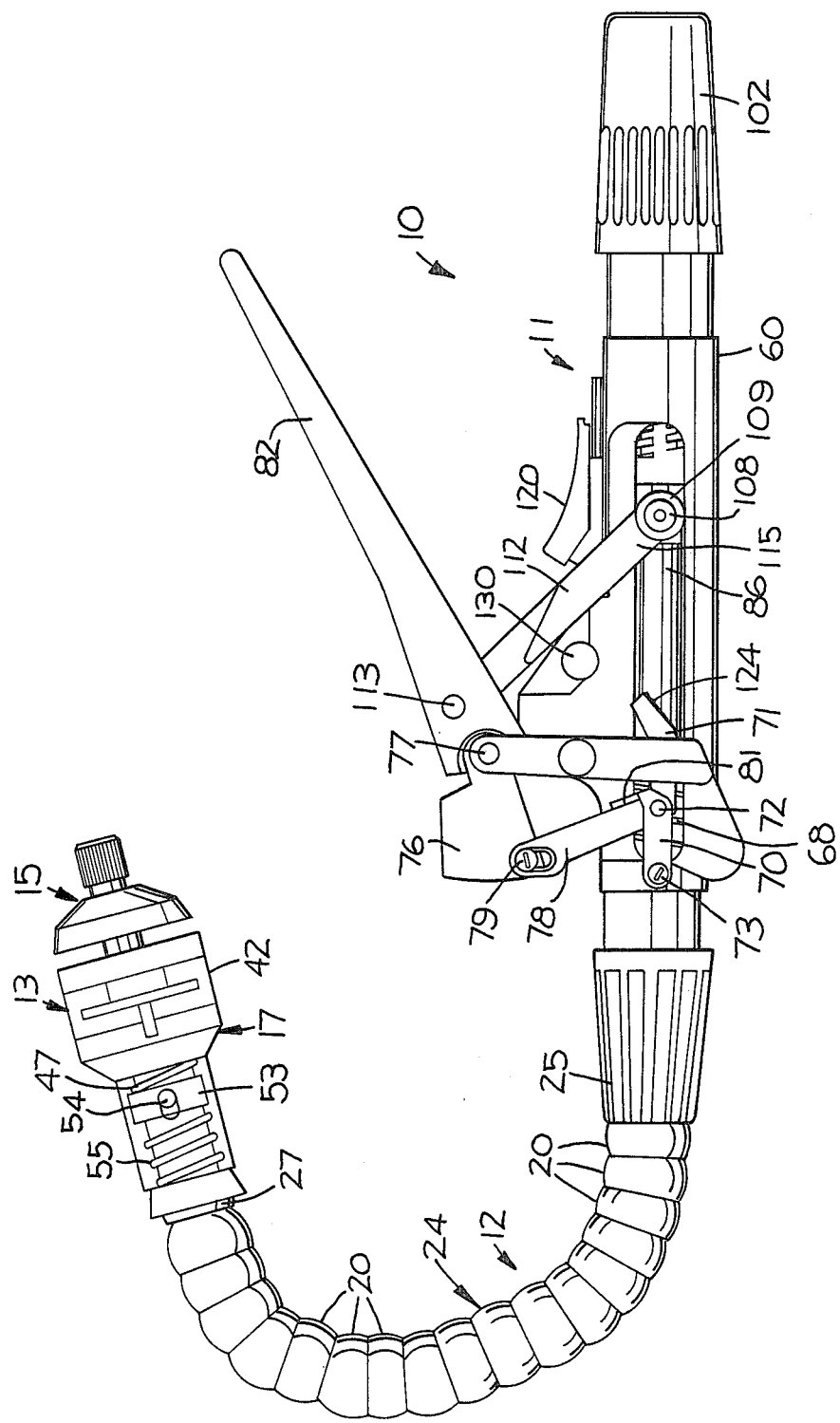

To use the stapler 10 (assuming the piston 66 and carrier 86 in the actuator assembly 11 are initially in their release positions and the slide 120 is in its non stapling position as shown in FIG. 4) a user first attaches the stapler subassembly 12 to the actuator assembly 11 by engaging the collar 34 from the stiffening assembly 28 and lug 39 from the cable assembly 36 of the stapler sub assembly 12 in the receptacle 67 in the piston 66 and the recess 87 of the carrier 86, respectively. The user then rotates the knob 102 to move the anchor member 89 by threaded engagement therewith and thereby moves the carrier 86 because of the screw 92 therebetween toward the engaged positions of the carrier 86 within the frame 60 (FIGS. 5-9) at which the lug 39 is retained in the recess 87. Such movement of the carrier 86 affords movement of the piston 66 under the influence of the spring 68 to its engaged position within the frame 60 at which the collar 34 is retained in the receptacle 67. Also, such movement positions the end surface 59 of the frustoconical member 25 in the spine structure 24 against the annular abutment portion 61 of the frame and causes the teeth 62 on the frame 60 to engage teeth 63 on the frustoconical member 25 to establish the rotational relationship between the actuator assembly 11 and stapler sub assembly 12. The stapler 10 is then ready for use. The user can allow the spine structure 24 to be flexible while he establishes a desired orientation between the head assembly 17 and the actuator assembly 11 for the particular task or operation he is undertaking, and then, if he desires, he may cause the spine structure 24 to rigidify by moving the actuating lever 82 from its outer normal position to its inner actuated position (FIG. 6). Such movement of the actuating lever 82 through contact at the surfaces 83 with the release member 76 causes pivoting of the release member 76 from its release to its engaged position which through the attaching links 78 causes movement of the toggle members 70 and 71 from their release to their engaged positions to move the piston 66 and thereby tension the stiffening assembly 28 to compress the spine segments 20 between the base member 27 of the staple holding assembly 13 and the frame 60 to thereby rigidify the spine structure 24. If the operator then again wants the spine structure 24 to be made flexible he can press the release member 76 to its release position (FIG. 5) to which it moves independent of the actuating lever 82 so that through the attaching links 78 the toggle members 70 and 71 are moved to their release positions and tension is removed from the stiffening assembly 28. The operator can also rotate the knob 102 to adjust the spacing between the end surface 45 of the staple holding assembly 13 and the anvil assembly 15 by movement of the carrier 86 along various of its open positions to facilitate positioning tissues to be stapled therebetween. When the tissues are properly positioned, the operator rotates the knob 102 to move the anchor member 89 fully to its first position (FIGS. 7-9) which, because of the screw 92 that limits relative movement between the anchor member 89 and carrier 86, positions the carrier 86 in its ready position and thereby the staple holding assembly 13 and anvil assembly 15 in their predetermined spaced position. The operator can then apply the staples to the tissue by moving the slide 120 from its non stapling position (FIGS. 4-7) to its stapling position (FIGS. 7-9) which through "the basses 122 " orients the end portions 115 of the yoke 112 adjacent the bosses 108. Subsequently, the operator can move the actuating lever 82 toward the frame 60 from its normal to its actuated position (FIG. 9) so that the yoke 112 drives the bosses 108 to move the carrier 86 to its final position which through the cable assembly 36 moves the staple holding assembly 13 and anvil assembly 15 to their closed position to close the staples 14 in the tissue therebetween, which produces an audible sound as the lip 56 on the base member 27 enters the recess 64 signalling to the user that the stapling is complete. The user then releases the actuating lever to its normal position, allowing the slide 120 to return to its non stapling position, and rotates the knob 102 to move the carrier 86 to its open position to thereby space the anvil assembly 15 from staple holding assembly 13 so that the head assembly 17 can be removed from the stapled tissue. The stapler sub assembly 12 can then be removed from the actuator assembly 11 by further rotating the knob 102 to move the carrier 86 to its release position (FIG. 4), which requires depression of the safety button 130 and results in the bosses 108 contacting the cam surfaces 124 on the toggle members 70 and 71 should they be in their engaged positions to move them to their release positions, and the carrier 86 contacting the piston 66 to move it against the bias of the spring 68 to its release position with the carrier 86. The used stapler subassembly 12 can then be removed.

The present invention has now been described with reference to one embodiment thereof. It will be apparent to those skilled in the art that many changes can be made in the embodiment described without departing from the scope of the present invention. Thus the scope of the present invention should not be limited to the structure descried in this application, but only by structures described by the language of the claims and the equivalents of those structures.

We claim:

1. A stapler subassembly comprising:
    a staple holding member adapted to hold a plurality of staples in a predetermined pattern;
    an anvil member having a forming surface adapted to be engaged with staples held in said staple holding member to bend said staples closed;
    means mounting said staple holding member and said anvil member for relative movement from at least one spaced position affording the positioning of tissue to be joined between said members toward a closed position to drive the staples through the tissues and bend closed the staples driven through the tissues;
    a plurality of rigid spine segments, each of said spine segments having a concave end surface, an opposite convex end surface, and a through opening between said end surfaces, said spine segments being disposed in end to end relationship with their openings aligned and the concave and convex surfaces of adjacent spine segments in engagement to form a spine structure extending from a first end to a second end abutting one of said members;
    a flexible stiffening assembly having a through passageway and extending through the aligned openings in the spine segments of said spine structure, said stiffening assembly having a second end attached to the member abutted by said spine structure, and a first end adjacent the first end of said spine structure and adapted to be tensioned relative to said spine structure to afford compressing the spine segments of said spine structure together to rigidify said spine structure; and
    a flexible cable assembly extending through the passageway in said stiffening assembly, said cable assembly having a second end attached to the member not abutted by said spine structure, and a first end adjacent the first end of said spine structure and adapted to be pulled relative to said spine structure to move said members to said closed position.

2. A stapler subassembly according to claim 1 wherein the end surfaces of said spine segments are spherically convex or concave.

3. A stapler subassembly according to claim 1 wherein said stiffening assembly comprises a woven wire tubular sleeve and spaced rigid tubular support members within said sleeve.

4. An actuator assembly adapted to be used with a stapler subassembly comprising a staple holding member adapted to hold a plurality of staples in a predetermined pattern; an anvil member having a forming surface adapted to be engaged with staples held in said staple holding member to bend said staples closed; means mounting said staple holding member and said anvil member for relative movement from at least one spaced position affording the positioning of tissue to be joined between said members toward a closed position to drive the staples through the tissues and bend closed the staples driven through the tissues; a plurality of rigid spine segments, each of which spine segments has a concave end surface, an opposite convex end surface, and a through opening between said end surface, said spine segments being disposed in end to end relationship with said through openings aligned and the concave and convex surfaces of adjacent spine segments in engagement to form a spine structure extending from a first end to a second end abutting one of said members; a flexible stiffening assembly having a through passageway and extending through the openings of said spine segments, said stiffening assembly having a second end attached to the member abutted by said spine structure, a first end adjacent the first end of said spine structure, and a collar at said first end; and a flexible cable assembly extending through the passageway in said stiffening assembly, said cable assembly having a second end attached to the member not abutted by said spine structure, and a first end adjacent the first end of said spine structure, said actuator assembly comprising:
    a frame adapted to abut the first end of said spine structure;
    manually actuatable member operating means including means adapted for releasably engaging the first end of said cable assembly and mounted on said frame for movement from an open position to position the members at their spaced position, to a closed position to move the members to their closed position; and
    manually activatable tension applying means adapted to releasably engage the first end of said stiffening assembly and mounted on said frame for movement from a disengaged position at which sufficient slack is provided in said stiffening assembly to afford flexing of said spine structure to orient said spine segments and thereby said anvil and staple holding members at a desired orientation relative to said actuator assembly, to an engaged position at which tension is applied to the first end of said stiffening assembly relative to said frame to compress the spine segments between the member abutting the second end of said spine structure and said frame and thereby rigidify said spine structure, comprising
        a piston having an axis and having wall means for defining a receptacle adapted to receive said collar with the through opening in said stiffening assembly aligned with said axis and for preventing movement of said collar axially of said piston when said collar is in said receptacle,
        said frame having a socket opening through the portion of said frame adapted to abut said spine structure and receiving said piston for axial movement within said socket from a release position with the walls of said piston defining said receptacle projecting from said frame to afford access to said receptacle, to engaged positions with the walls of said piston defining said receptacle within said socket so that said collar is retained in said receptacle,
        at least one pair of toggle members having first ends pivotably attached together at a central axis and opposite second ends with the second end of one of said toggle members pivotably mounted on said frame, and the second end of the other of said toggle members pivotably mounted on said piston, said toggle members being mounted for movement between various release positions with the pivotably mounted first and second ends of said toggle members out of alignment to afford movement of said piston between said release position and said engaged positions, to an engaged position with the pivotably mounted first and second ends of said toggle members generally aligned to forcibly move said piston to a tensioning position at which tension can be applied to said stiffening assembly through said collar, a release member mounted on said frame for pivotable motion about a pivot axis, an actuating link having a first end pivotably attached to said toggle members at said central axis and a second end pivotably mounted on said release member at a position spaced from said pivot axis, said release member being mounted on said frame for movement between an engaged position with said release member positioning said toggle members in their engaged position, and release positions to which said release member can be manually pushed with said toggle member in their release positions, a manually operable actuating lever mounted on said frame for pivotable movement between a normal position and an actuated position, and means adapted for engagement between said actuating lever and said release member for moving said release member to said engaged position upon movement of said actuating lever from said normal position to said actuated position, for affording retention of said release member in said engaged position upon movement of said actuating member from said actuated position to said normal position and for affording free movement of said release member between said engaged and release positions when said actuating lever is in said normal position.

5. A stapler according to claim 4 wherein said staple holding member includes means for producing an audible signal when said members are moved to said closed position.

6. An actuator assembly according to claim 4 wherein said flexible cable assembly has a lug at said first end and said manually actuatable member operating means including means adapted for releasably engaging the first end of said cable assembly and mounted on said frame for movement from open positions to position the members at their spaced positions, to a closed position to move the members to their closed position comprises a carrier having an axis and having wall means for defining a recess adapted to receive said lug with the activating cable aligned with said axis and for preventing movement of said lug axially of said carrier when said lug is in said recess, means including said piston for defining a passageway adapted to receive said carrier opening through the portion of said frame adapted to abut said spine structure, said carrier being mounted for axial movement within said passageway from a release position with the walls of said carrier defining said recess projecting from said passageway to afford access to said recess in said carrier, to engaged positions with the walls of said carrier defining said recess within said means defining said passageway so that said lug is retained in said recess, said engaged position including a plurality of open positions affording positioning said staple holding and anvil members at various spaced positions to afford positioning tissues there between, a ready position adapted to position said members at a predetermined spaced position, and a final position adapted to position said members at said closed position, and manually activatable means for positioning said carrier in said release and engaged positions including an anchor member having an axis and a threaded periphery along said axis, said carrier being mounted on said frame for axial movement along a path axially aligned with said carrier at the end of said carrier opposite said recess, relative movement limiting means in engagement between said carrier and said anchor member for affording limited relative axial movement between said carrier and said anchor over a distance about equal to the distance between said ready and final positions of said carrier, means for preventing rotation of said anchor member relative to said frame, an adjustment knob having an axis and a bore around said axis defined by internal threads in engagement with the threads on said anchor member, means for mounting said adjustment knob on said frame for rotation about said axis while preventing axial movement of said adjustment knob relative to said frame, said adjustment knob being manually rotatable to move said anchor member from a first position at which said movement limiting means affords movement of said carrier between said ready and said final positions to second positions to thereby move said carrier to said open and engaged positions, and manually activatable pressure applying means mounted on said frame adapted for engaging said carrier in said ready position when said anchor member is in said first position and for moving said carrier from said ready position to said final position to move said members to said closed position.

7. An actuator assembly according to claim 6 further including means for moving said toggle members to said release positions from said engaged position upon movement of said carrier from said engaged positions to said release position.

8. An actuator assembly according to claim 6 wherein said manually activatable pressure applying means mounted on said frame adapted for engaging said carrier in said ready position when said anchor member is in said first position and for moving said carrier from said ready position to said final position to move said members to said closed position comprises a pair of opposite outwardly projecting bosses on said carrier, said actuating lever, a yoke having a first end portion pivotably mounted on said actuating lever about an axis spaced from said pivot axis, and second end portions adapted to engage said bosses, and means for guiding said second end portions manually movable between a non-stapling position spaced from said bosses, and a stapling position aligned with said bosses to move said carrier from said ready position to said final position upon movement of said actuating lever from aaid normal to said actuated position.

9. An actuator assembly according to claim 8 wherein said means for guiding comprises
a manually operable slide slidably mounted on said frame and
means for connecting said yoke to said slide so that manual moment of said slide moves said second end portions between said stapling and non-stapling positions.

10. An actuator assembly according to claim 8 further including means for moving said toggle members to said release positions from said engaged position upon movement of said carrier from said engaged positions to said release position comprising a cam on one of said toggle members adapted for engagement by said boss.

11. An actuator assembly adapted to be used with a stapler subassembly comprising a staple holding member adapted to hold a plurality of staples in a predetermined pattern; an anvil member having a forming surface adapted to be engaged with staples held in said staple holding member to bend said staples closed; means mounting said staple holding member and said anvil member for relative movement from at least one spaced position affording the positioning of tissue to be joined between said members toward a closed position to drive the staples through the tissues and bend closed the staples driven through the tissues; a plurality of rigid spine segments, each of which spine segments has a concave end surface, an opposite convex end surface, and a through opening between said end surfaces, said spine segments being disposed in end to end relationship with said through openings aligned and the concave and convex surfaces of adjacent spine segments in engagement to form a spine structure extending from a first end to a second end abutting one of said members; a flexible stiffening assembly having a through passageway and extending through the openings of said spine segments, said stiffening assembly having a second end attached to the member abutted by said spine structure, and a first end adajacent the first end of said spine structure; and a flexible cable assembly extending through the passageway in said stiffening assembly, said cable assembly having a second end attached to the member not abutted by said spine structure, a first end adjacent the first end of said spine structure, and a lug at said first end, said actuator assembly comprising:
a frame adapted to abut the first end of said spine structure;
manually activatable tension applying means adapted to releasably engage the first end of said stiffening assembly and mounted on said frame for movement from a disengaged position at which sufficient slack is provided in said stiffening assembly to afford flexing of said spine structure to orient said spine segments and thereby said anvil and staple holding members at a desired orientation relative to said actuator assembly, to an engaged position at which tension is applied to the first end of said stiffening assembly relative to said frame to compress the spine segments between the member abutting the second end of said spine structure and said frame and thereby rigidify said spine structure; and
manually actuatable member operating means including means adapted for releasably engaging the first end of said cable assembly and mounted on said frame for movement from an open position to position the members at their spaced position, to a closed position to move the members to their closed position, said manually actuatable member operating means comprising
a carrier having an axis and wall means for defining a recess adapted to receive said lug with the cable assembly aligned with said axis and for preventing movement of said lug axially of said carrier when said lug is in said recess,
means defining a passageway adapted to receive said carrier opening through the portion of said frame adapted to abut said spine structure, said carrier being mounted for axial movement within said passageway from a release position with the walls of said carrier defining said recess projecting from said passageway to afford access to said recess in said carrier, to engaged positions with the walls of said carrier defining said recess within said means defining said passageway so that said lug is retained in said recess, said engaged positions including a plurality of open positions affording positioning said staple holding and anvil members at various spaced positions to afford positioning tissues there between, a ready position adapted to position said members at a predetermined spaced position, and a final position adapted to position said members at said closed position, and
manually activatable means for positioning said carrier in said release and engaged positions including
an anchor member having an axis and a threaded periphery along said axis, said carrier being mounted on said frame for axial movement along a path axially aligned with said carrier at the end of said carrier opposite said recess,
relative movement limiting means in engagement between said carrier and said anchor member for affording limited relative axial movement between said carrier and said anchor over a distance about equal to the distance between said ready and final positions of said carrier,
means for preventing rotation of said anchor member relative to said frame,
an adjustment knob having an axis and a bore around said axis defined by internal threads in engagement with the threads on said anchor member,
means for mounting said adjustment knob on said frame for rotation about said axis while preventing axial movement of said adjustment knob relative to said frame, said adjustment knob being manually rotatable to move said anchor member from a first position at which said movement limiting means affords movement of said carrier between said ready and said final positions to second positions to thereby move said carrier to said open and release positions, and
manually activatable pressure applying means mounted on said frame adapted for engaging said carrier in said ready position when said anchor member is in said first position and for moving said carrier from said ready position to said final position to move said members to said closed position.

12. An actuator assembly according to claim 11 wherein said manually activatable pressure applying means mounted on said frame adapted for engaging said carrier in said ready position when said anchor member is in said first position and for moving said carrier from said ready position to said final position to move said members to said closed position comprises
- a pair of opposite outwardly projecting bosses on said carrier,
- an actuating lever mounted on said frame for pivotal movement about a pivot axis from a normal position to an actuated position,
- a yoke having a first end portion pivotably mounted on said actuating lever about an axis spaced from said pivot axis, and second end portions adapted to engage said bosses, and
- means for guiding said second end portions manually movable between a non-stapling position spaced from said bosses, and a stapling position aligned with said bosses to move said carrier from said ready position to said final position upon movement of said actuating lever from said normal to said actuated position.

13. An actuator assembly according to claim 12 wherein said means for guiding comprises
- a manually operable slide slidably mounted on said frame, and and
- means for connecting said yoke to said slide so that manual moment of said slide moves said end portions between said stapling and non-stapling positions.

14. An actuator assembly according to claim 11 further including manually releasable means for preventing movement of said carrier from said engaged positions to said release position by operation of said adjustment knob to restrict inadvertent movement of said carrier to said release position.

15. A stapler including;
- a staple holding member adapted to hold a plurality of staples in a predetermined pattern;
- an anvil member having a forming surface adapted to be engaged with staples held in said staple holding member to bend said staples closed;
- means mounting said staple holding member and said anvil member for relative movement from at least one spaced position affording the positioning of tissue to be joined between said members toward a closed position to drive the staples through the tissues and bend closed the staples driven through the tissues;
- a plurality of rigid spine segments, each of said spine segments having a concave end surface, an opposite convex end surface, and a through opening between said end surfaces, said spine segments being disposed in end to end relationship with their openings aligned and the concave and convex surfaces of adjacent spine segments in engagement to form a spine structure extending from a first end to a second end abutting one of said members;
- a flexible stiffening assembly having a through passageway and extending through the aligned openings in the spine segments of said spine structure, said stiffening assembly having a second end attached to the member abutted by said spine structure, and a first end adjacent the first end of said spine structure;
- a flexible cable assembly extending through the passageway in said stiffening assembly, said cable assembly having a second end attached to the member not abutted by said spine structure, and a first end adjacent the first end of said spine structure;
- a frame abutting the first end of said spine structure;
- manually activatable tension applying means engaging the first end of said stiffening assembly and mounted on said frame for movement from a disengaged position at which sufficient slack is provided in said stiffening assembly to afford flexing of said spine structure to orient said spine segments and thereby said anvil and staple holding members at a desired orientation relative to said actuator assembly, to an engaged position at which tension is applied to the first end of said stiffening assembly relative to said frame to compress the spine segments between the member abutting the second end of said spine structure and said frame and thereby rigidify said spine structure; and
- manually actuatable member operating means including means engaging the first end of said cable assembly and mounted on said frame for movement from an open position to position the members at their spaced position, to a closed position to move the members to their closed position.

16. A stapler according to claim 15 wherein the end surfaces of said spine segments are spherically convex or concave.

17. A stapler according to claim 15 wherein said stiffening assembly comprises a woven wire tubular sleeve and spaced rigid tubular support members within said sleeve.

18. A stapler according to claim 15 wherein
said manually activatable tension applying means engaging the first end of said stiffening assembly comprises a piston having an axis engaged with said stiffening assembly,
said frame has a socket receiving said piston for axial movement within said socket, and
said manually activatable tension applying means comprises
said piston, and
at least one pair of toggle members having first ends pivotably attached together at a central axis and opposite second ends with the second end of one of said toggle members pivotably mounted on said frame, and the second end of the other of said toggle members pivotably mounted on said piston,
said toggle members being mounted for movement between various release positions with the pivotably mounted first and second ends of said toggle members out of alignment, to an engaged position with the pivotably mounted first and second ends of said toggle members generally aligned to forcibly move said piston to a tensioning position at which tension is applied to said stiffening assembly.

19. A stapler according to claim 18 wherein said manually activatable tension applying means further comprises
a release member mounted on said frame for pivotable motion about a pivot axis,
an actuating link having a first end pivotably attached to said toggle emmbers at said central axis and a second end pivotably mounted on said release member at a position spaced from said pivot axis,
said release member being mounted on said frame for movement between an engaged position with said release member positioning said toggle members in their engaged position, and release positions to which said release member can be manually pushed with said toggle members in their release positions, a manually operable actuating lever mounted on said frame for pivotable movement between a normal position and an actuated position, and means adapted for engagement between said actuating lever and said release member for moving said release member to said engaged position upon movement of said actuating lever from said normal position to said actuated position, for affording retention of said release member in said engaged position upon movement of said actuating member from said actuated position to said normal position and for affording free movement of said release member between said engaged and release positions when said actuating lever is in said normal position.

20. A stapler according to calim 19 wherein said manually actuatable member operating means engaging the first end of said cable assembly comprises a carrier having an axis and means including said piston for defining a passageway adapted to receive said carrier opening through the portion of said frame adapted to abut said spine structure, said carrier being mounted for axial movement within said passageway to a plurality of open positions affording positioning said staple holding and anvil members at various spaced positions to afford positioning tissues there between, a ready position adapted to position said members at a predetermined spaced position, and a final position adapted to position said members at said closed position, and manually activatable means for positioning said carrier in said open ready and final positions including an anchor member having an axis and a threaded periphery along said axis, said carrier being mounted on said frame for axial movement along a path axially aligned with said carrier at the end of said carrier opposite said recess, relative movement limiting means in engagement between said carrier and said anchor member for affording limited relative axial movement between said carrier and said anchor over a distance about equal to the distance between said ready and final positions of said carrier, means for preventing rotation of said anchor member relative to said frame, an adjustment knob having an axis and a bore around said axis defined by internal threads in engagement with the threads on said anchor member, means for mounting said adjustment knob on said frame for rotation about said axis while preventing axial movement of said adjustment knob relative to said frame, said adjustment knob being manually rotatable to move said anchor member from a first position at which said movement limiting means affords movement of said carrier between said ready and said final positions to second positions to thereby move said carrier to said open positions, and manually activatable pressure applying means mounted on said frame adapted for engaging said carrier in said ready position when said anchor member is in said first position and for moving said carrier from said ready position to said final position to move said members to said closed position.

21. A stapler according to calim 20 wherein said manually activatable pressure applying means mounted on said frame adapted for engaging said carrier in said ready position when said anchor member is in said first position and for moving said carrier from said ready position to said final position to move said members to said closed position comprises a pair of opposite outwardly projecting bosses on said carrier, said actuating lever, a yoke having a first end portion pivotably mounted on said actuating lever about an axis spaced from said pivot axis, and second end portions adapted to engage said bosses, and means for guiding said second end portions manually movable between a non-stapling position spaced from said bosses, and a stapling position aligned with said bosses to move said carrier from said ready to said final position upon movement of said actuating lever from said normal to said actuated position.

22. A stapler according to claim 21 wherein said means for guiding comprises a manually operable slide slidably mounted on said frame, and means for connecting said yoke to said slide so that manual moment of said slide moves said end portions between said stapling and non-stapling positions.

* * * * *

UNITED STATES PATENT AND TRADEMARK OFFICE
CERTIFICATE OF CORRECTION

PATENT NO. : 4,754,909

DATED : July 5, 1988

INVENTOR(S) : John M. Barker and Alan K. Plyley

It is certified that error appears in the above-identified patent and that said Letters Patent is hereby corrected as shown below:

Col. 12, line 46, before "comprising" insert --said manually activatable tension applying means--.

Col. 15, line 3, "aaid" should read --said--.

Col. 15, line 43, "adajacent" should read --adjacent--.

Col. 19, line 21, "calim" should read --claim--.

Signed and Sealed this

Twenty-sixth Day of December, 1989

Attest:

JEFFREY M. SAMUELS

Attesting Officer     Acting Commissioner of Patents and Trademarks